United States Patent [19]
Wilson et al.

[11] Patent Number: 5,538,014
[45] Date of Patent: Jul. 23, 1996

[54] DEFORMABLE FACE SHIELD WITH MOUTHPIECE

[75] Inventors: Dorothy E. Wilson; James W. Wilson, both of 9351 SW. 23rd St., #3303, Fort Lauderdale, Fla. 33324; Michael R. Weber, Tampa, Fla.

[73] Assignees: James W. Wilson; Dorothy E. Wilson, both of Fort Lauderdale, Fla.

[21] Appl. No.: 324,699

[22] Filed: Oct. 18, 1994

Related U.S. Application Data

[63] Continuation-in-part of Ser. No. 179,423, Jan. 10, 1994, Pat. No. 5,503,167.

[51] Int. Cl.$^6$ ................................................ A61B 19/00
[52] U.S. Cl. ........................................ 128/863; 132/319
[58] Field of Search ........................... 2/9, 174, 206; 132/319; 128/863

[56] References Cited

U.S. PATENT DOCUMENTS

| | | | |
|---|---|---|---|
| 704,311 | 7/1902 | Galley | 128/863 |
| 3,015,105 | 1/1962 | Rogowski | 2/174 |
| 3,041,624 | 7/1962 | Cutrona, Jr. | 2/206 |
| 3,060,445 | 10/1962 | Brockman | 2/9 |
| 3,103,667 | 9/1963 | Rogowski | 2/174 |
| 3,602,913 | 9/1971 | Neese | 2/9 |
| 3,772,707 | 11/1973 | Alosi et al. | 2/174 |
| 3,828,366 | 8/1974 | Conrad et al. | 2/174 |
| 4,133,052 | 1/1979 | Hodgman et al. | 2/174 |
| 4,223,407 | 9/1980 | Zappala | 2/174 |
| 5,088,485 | 2/1992 | Schock | 128/202.28 |

FOREIGN PATENT DOCUMENTS 2013772  12/1971  Germany .............................. 132/319

*Primary Examiner*—Aaron J. Lewis
*Attorney, Agent, or Firm*—Malin, Haley, DiMaggio & Crosby

[57] ABSTRACT

A transparent, flexible and deformable face shield that adaptably fits and conforms to the contours of the wearer's face to protect the wearer's eyes, contact lenses, face, etc. from hair spray products or other products containing contaminants. The face shield includes an inwardly projecting mouthpiece which is gripped between the wearer's teeth to hold the shield in sealing engagement over the wearer's face, leaving both of the wearer's hands free to perform hairstyling or other functions. The face shield may also include additional attachments for covering the forehead, ears or cheeks when the mask falls short of these areas.

19 Claims, 6 Drawing Sheets

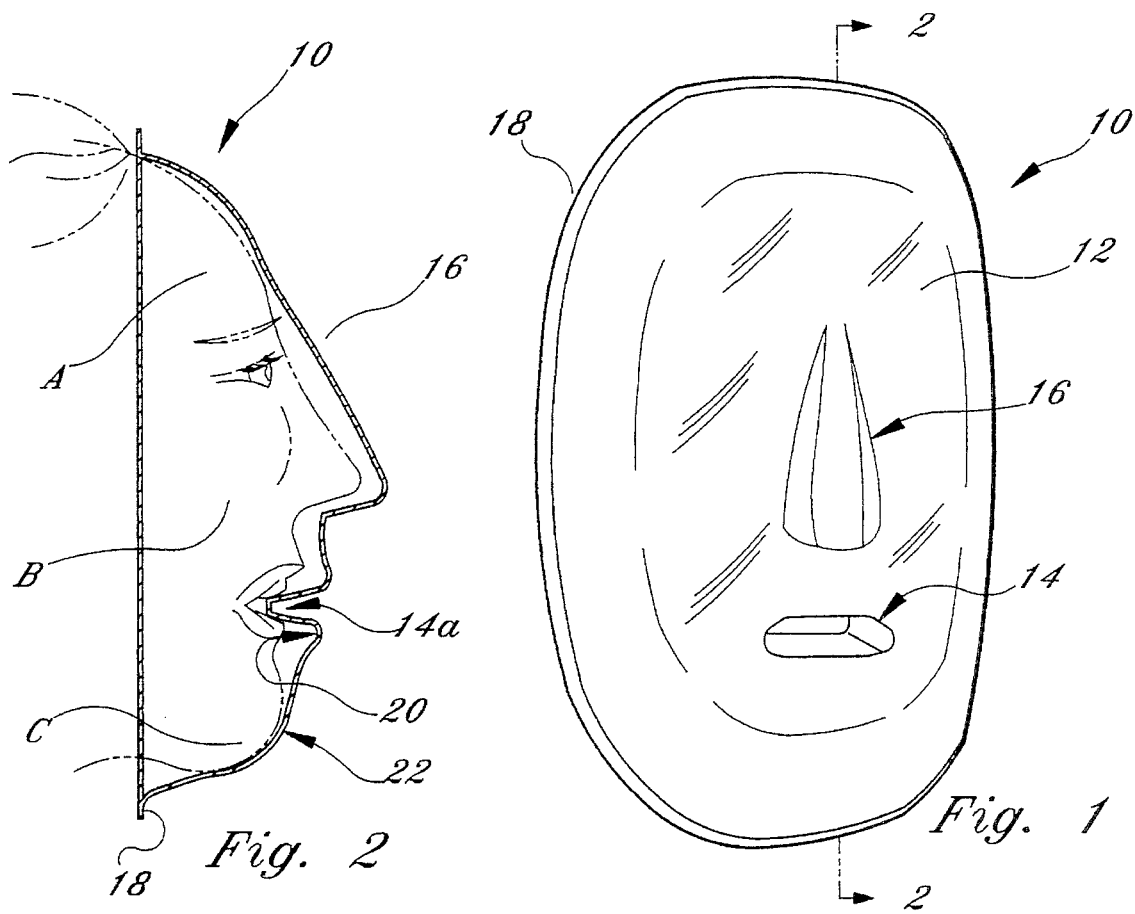
Fig. 1
Fig. 2
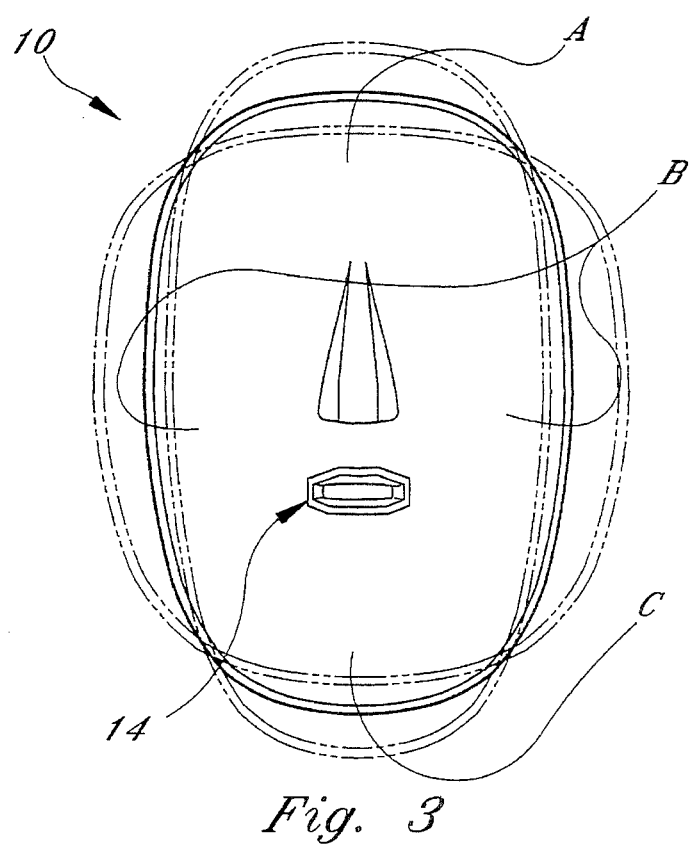
Fig. 3

DEFORMABLE FACE SHIELD WITH MOUTHPIECE

This application is a continuation-in-part of co-pending application Ser. No. 08/179,423 filed Jan. 10, 1994, U.S. Pat. No. 5,503,167, entitled "Deformable Face Shield With Mouthpiece."

BACKGROUND OF THE INVENTION

1. Field of the Invention

The instant invention is directed to a device adapted to cover and protect a wearer's face and respiratory tract from airborne hairstyling products, contaminants or the like. Specifically, the invention is directed to a deformable face shield having a mouthpiece for holding the shield in sealing engagement over the wearer's face without requiring the wearer to hold the shield in place. The shield protects the wearer's eyes, face and respiratory tract from hair spray products or other airborne matter without inhibiting the wearer's ability to style his or her hair using one or both hands or to perform other tasks requiring the use of one or both of the wearer's hands.

2. Description of the Background Art

It is undisputed and widely recognized that hairstyling products, such as hair spray, are harmful to the eyes and damaging to contact lenses. Documented research reveals that direct exposure of hair spray to the eye can result in keratitis, an inflammation of the cornea of the eye. Further, hair spray clogs the pores of permeable contact lenses, interfering with the oxygen supply to the cornea, which can result in corneal ulcers and blurred vision. Hair spray contaminates contact lenses and causes them to become "sticky" or "tacky", preventing them from moving freely on the wearer's eye, resulting in dryness and irritation to the cornea. Consequently, hair spray products contain warning labels such as " . . . do not spray in the eyes . . . " or ". . . do not use near the eyes. . . . " Since it is virtually impossible to use hair spray without spraying in or around the eyes, eye care professionals recommend that hair spray users close their eyes while spraying. It is also advised that contact lenses not be inserted until hair spray use is completed.

Previously, the only protective devices available for hairstyling were either hand-held shields or goggles. Not surprisingly, these devices interfere with the hairstyling process. Hand-held shields do not provide a snug, contoured fit on the wearer's face, and they cannot be conveniently used since hairstyling usually requires the wearer to use both hands. Goggles and other conventional face protecting shields employ bands or cords, or they require earpieces, that extend into the hairline. These conventional devices are inconvenient since they interfere with the wearer's hair styling. In addition, these devices do not easily conformto a wide variety of face shapes and sizes, nor do they provide a snug fit to protect the wearer's eyes, face and respiratory tract. Although some attempts have been made to alleviate the above-noted problems, none have met with success or widespread approval.

Neese (U.S. Pat. No. 3,602,913) discloses an apparatus to protect the wearer's face from hair spray. Specifically, the reference discloses a one-piece molded mask with protective eye openings, a chin portion and a handle for holding the mask in place using one hand. The eyes are left exposed through the eye opening and the mask is opaque, making it difficult for the user to see what he or she is doing. In order to prevent hair spray from entering through the eye openings, the user must be extremely careful not to spray in or around the eye openings. Neese also discloses an embodiment without a handle, having inward-projecting tabs grasped in the mouth of the wearer. However, the tabs do not allow the wearer to control, nor do they have an effect on, the contour and fit of the mask against the face. In fact, the mask is rigid and cannot conform to various face shapes and sizes.

Another face shield is disclosed by Rogowski in U.S. Pat. No. 3,015,105. Rogowski '105 discloses a semi-rigid, form-fitting safety mask for shielding a person's face during beauty treatments or industrial tasks. This safety mask provides a channel for receiving the wearer's nose, the channel defining a passage for air. Earpieces are provided for holding the mask on the wearer's face. Rogowski's mask is semi-rigid, and it therefore cannot be easily adapted to fit all size faces.

It is apparent from the background art that there is still a need for a transparent shield that is conformable to a wide variety of faces and which can be worn without inhibiting the wearer's ability to style their own hair. The present invention solves these problems by providing a transparent, flexible shield having a mouthpiece by which the shield is securely and sealingly held against the wearer's face. In addition, alternate embodiments of the instant invention may employ various combinations of attachments such as a forehead cover and cheek guard for smaller shields, ear guard protectors for shielding the ear, or a hair net cover to safeguard styled hair while dressing.

SUMMARY OF THE INVENTION

It is an object of the present invention to provide a flexible, deformable face shield having a mouthpiece which is used to hold the shield in place on the wearer's face.

It is another object of the invention to provide a transparent face shield that allows the wearer to see clearly while performing various functions.

It is also an object of this invention to provide a flexible, deformable face shield that conforms to a wide variety of face shapes and sizes and that sealingly engages the face.

It is still another object of the invention to provide a face shield with an open mouthpiece and a filter for filtering out pollutants, irritants or the like.

It is a further object of the invention to provide a face shield with additional cover attachments for shielding the cheeks, ears, or hair.

In accordance with these and other objects, the present invention comprises a flexible and deformable face mask shield molded into a concave shell having an inwardly protruding mouthpiece or bite plate and an outwardly projecting nose channel, the shield functioning as a form-fitting mask. Inherent in the face shield design is a unique flexibility that allows it to adapt to the contours of various face shapes and sizes. The shield may be deformed along at least three axes to achieve a snug fit around the brow and cheek areas of the face. The resilient characteristic or "memory" of the face shield allows it to return to its original shape when not being used. A plastic material such as vinyl, acrylic or other synthetic resin is used in manufacturing the shield so that it is transparent yet flexible and deformable. The inwardly protruding mouthpiece or bite plate may be formed integrally with the body of the shield, or as a separate piece, and this mouthpiece is used to hold the shield in place on the face when the wearer bites down on it, leaving the wearer's hands free for hairstyling or other activities. Since the shield is deformable and the mouthpiece is integral with, or attached to, the shield, a snug fit can be achieved by adjusting the position of the shield and biting down on the mouthpiece so that a tight seal is formed between the periphery of the shield and the wearer's face. With the shield in place, hairstyling products may be applied without contacting the wearer's eyes or face. The shield may also be worn while performing other tasks where protection of the face is necessary or desirable. Since the mask is preferably transparent, the wearer has full visibility.

In an alternate embodiment, the mouthpiece is provided with a breathing opening to the exterior of the shield and includes a filter for filtering inhaled air. In the alternative, a simple unfiltered air passage may be provided in the mouthpiece to allow the wearer to breathe through the shield. If commercial use is desired, the face shield may be formed from two pieces, the first piece comprising the face shield itself, and the second piece comprising a removable bite plate or bite plate cover which can be washed and/or sterilized.

In another embodiment, a forehead cover may be connected to the upper edge of the face shield to act as a hair spray deflector to prevent hair spray from contacting the forehead of a user in the event that the height of the face shield is insufficient to cover the forehead up to the hairline. The forehead cover can be sized and shaped to fit the particular wearer, and may even be cut to a desired size by the end user. The forehead cover is preferably flexible and constructed of the same or nearly the same material as the face shield. Means are provided for removably connecting the forehead cover to the face shield.

In other embodiments, cheek guards may be releasably attached to both sides of the face shield body to extend protection to uncovered areas of the cheek, ear cover protectors may be extended from the sides of the face shield to conceal the wearer's ears, or a hair net may be removably attached to the top end of the mask to cover styled hair before dressing so as to preserve the style. Any of these additional embodiments noted above may be used or incorporated together or in any combination for achieving complete protection of the face and head as desired or dictated by the wearer's preferences since these additional attachments may be removed.

BRIEF DESCRIPTION OF THE DRAWINGS

The invention is described in detail below with reference to the accompanying drawings, in which:

FIG. 1 is a perspective view of the preferred embodiment of the face shield of the invention;

FIG. 2 is a cross-sectional view of the face shield taken along line 2—2 of FIG. 1;

FIG. 3 is a plan view of the face shield in various stretched (deformed) and unstretched (non-deformed) positions;

DESCRIPTION OF THE PREFERRED EMBODIMENTS

Figure 4:
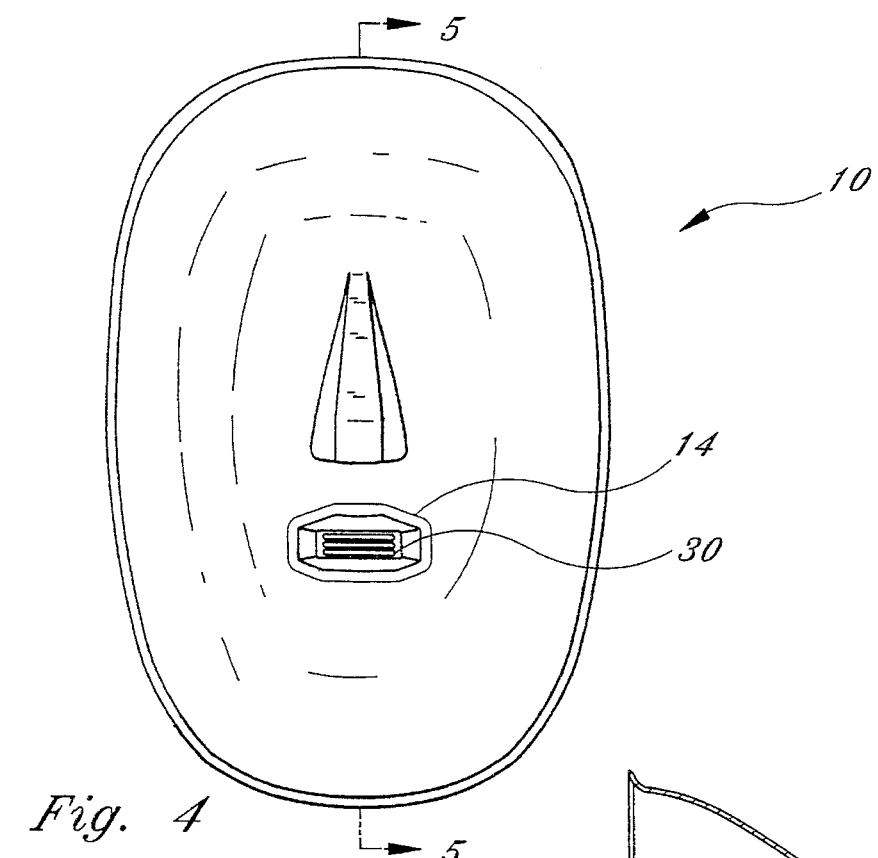
FIG. 4 is a perspective view of the face shield showing another embodiment having an air passageway without a filter.

FIGS. 1—7 show a face shield 10 having a face-fitting contour for protecting the wearer's eyes, contact lenses and face from airborne contaminants, such as hair spray. The shield 10 comprises a body 12, a separate or integrally formed mouthpiece 14 and a nose channel 16. The shield is manufactured or molded into a single concave shape having an outer edge defined by a lip 18. The body 12 of the face shield 10 is flexible along at least three planes (see FIG. 3) so that it can be made to conform to the contours of different faces, providing a suitable seal in all cases. The mouthpiece 14 protrudes inwardly from the interior surface 20 and is received in the wearer's mouth when the shield 10 is held against the wearer's face. As shown in FIG. 2, the mouthpiece 14 is tapered in cross-section and forms a cavity 14a which enhances the deformability and flexibility of face shield 10 when drawn into the mouth and allows the wearer to bite down and "fix" the shield in a form-fitting position over the wearer's face. The mouthpiece 14 may be any cross sectional shape without departing from the spirit and scope of the instant invention. Nose channel 16 is integrally formed with the face shield 10, and projects outwardly from the exterior surface 22 of the body 12, providing clearance for the nose. Such clearance is necessary so that the shield fits snugly to the face around the wearer's eye and cheek areas.

The face shield 10 may be fabricated from a single thin piece of thermoplastic material such as vinyl, acrylic or other synthetic resin. In the preferred embodiment, the face shield 10 is approximately 0.02 inches thick, but may have other dimensions without departing from the scope of the instant invention so long as it remains flexible. It is light, flexible and easily deformable, giving the shield three dimensional flexibility as shown in FIG. 3 so that it fits snugly to the brow, cheek and chin areas of the wearer. The uniform structure of the face shield 10 further facilitates mass production of the shield. Since the posterior edge 18 is defined in one plane a single rule die can be used to cut the shield from carrier sheets. The shield 10 may also be made by vacuum forming, blow molding or injection molding of a clear plastic material or the like. In a vacuum forming process, the mask forming material is heated to a thermoplastic state and then placed over a three-dimensional mold. Since thermoplastic materials have a "memory" which causes them to return to their original state, the resiliency of the material allows the face shield to retain its utility over time.

In use, the face shield 10 is placed on, and pressed firmly against, the wearer's face so that the brow, cheek and chin areas are in firm contact with the shield (at points A, B, and C, respectively, as shown in FIG. 1 and 3). Additional pressure may be placed on the shield to cause the lateral cheek areas B to move inwardly causing the mouthpiece 14 to move further into the wearer's mouth. As this external pressure is exerted on the body 12, face shield 10 conforms more closely to the contours of the face until, finally, the shield 10 is engaged against the wearer's face, at which time the bite plate or mouthpiece 14 is pinched between the wearer's teeth so the shield is maintained in sealing engagement around the wearer's face.

The mask is also suitable for use in connection with emergency medical situations, carpentry and other activities where protection is desired. In addition, the shield may be worn to protect clothes from cosmetics which often stain or smudge the garments when they are pulled over the wearer's head.

Figure 6:
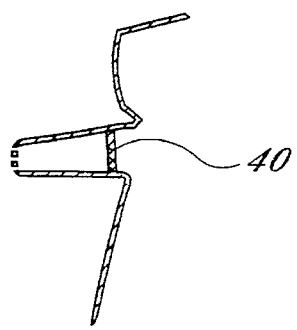
FIG. 6 is a cross-sectional view of the mouth cavity with a filter strip at the front.
Figure 5:
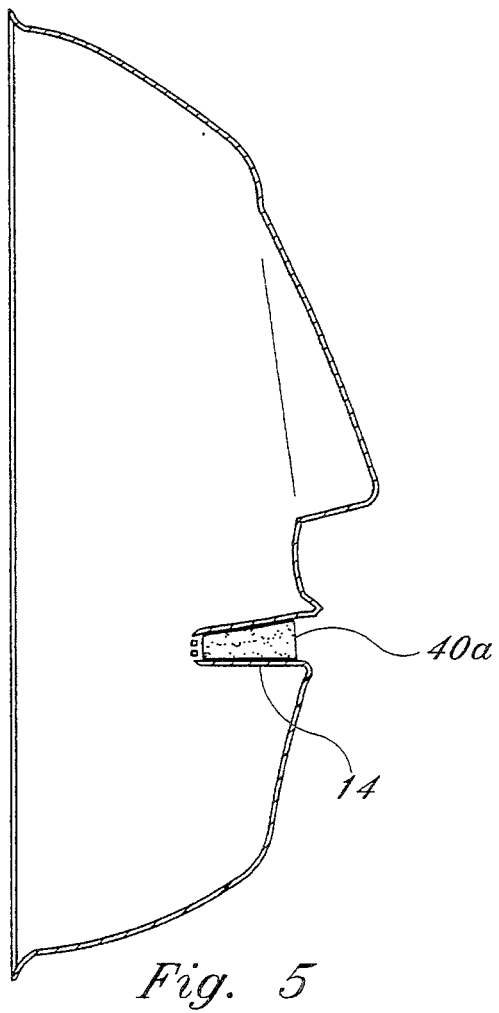
FIG. 5 is a cross-sectional view of the face shield taken along line 5—5 of FIG. 4 with a filter in the mouth cavity.

In the embodiment shown in FIG. 4, the mouthpiece 14 includes an air passageway 30 to allow the wearer to breathe through the mouthpiece 14 while wearing the shield 10. Referring to FIG. 5, the filter 40 may comprise a removable foam filter insert 40a made of a permeable membrane to allow breathing. Alternatively, the filter 40 may be secured in front of the cavity 14a with the use of pressure sensitive adhesives or the like as seen in FIG. 6.

Figure 7:
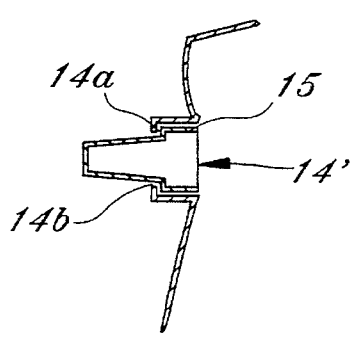
FIG. 7 is a cross-sectional view of the mouth cavity with a removable mouthpiece.

In an alternate embodiment, the mouthpiece may comprise a removable bite plate 14', shown in FIG. 7. The bite plate 14' mates with an aperture 14b defined by cavity 14a. A head 15 is formed at one end of the bite plate 14' which abuts the cavity 14a around the aperture 14b when inserted through the aperture 14b. The head 15 secures the mouthpiece in the cavity 14a and prevents it from passing completely through the aperture 14b.

Figure 8:
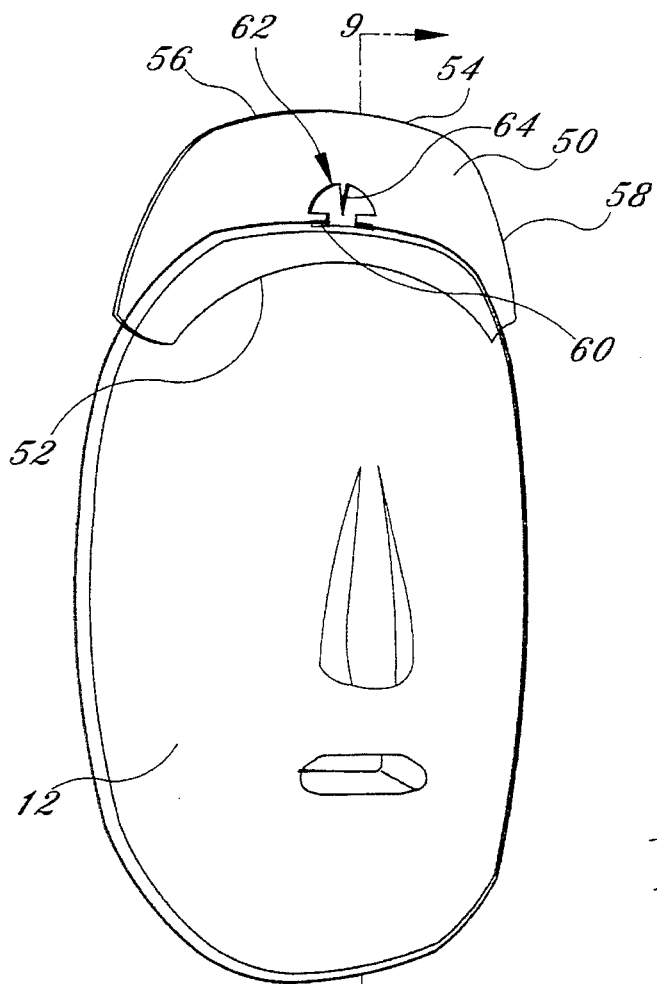
FIG. 8 is a perspective view of the face shield with a removable forehead cover connected thereto.
Figure 10:
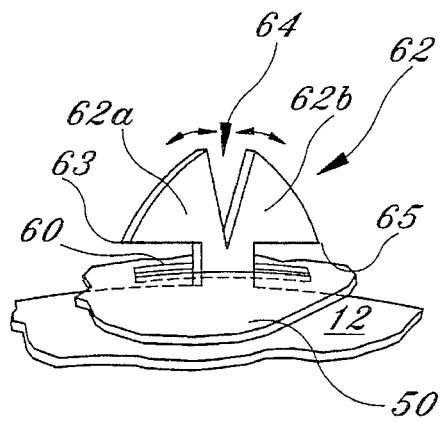
FIG. 10 is an enlarged view of the area of detail indicated by circle "10" of FIG. 9.
Figure 9:
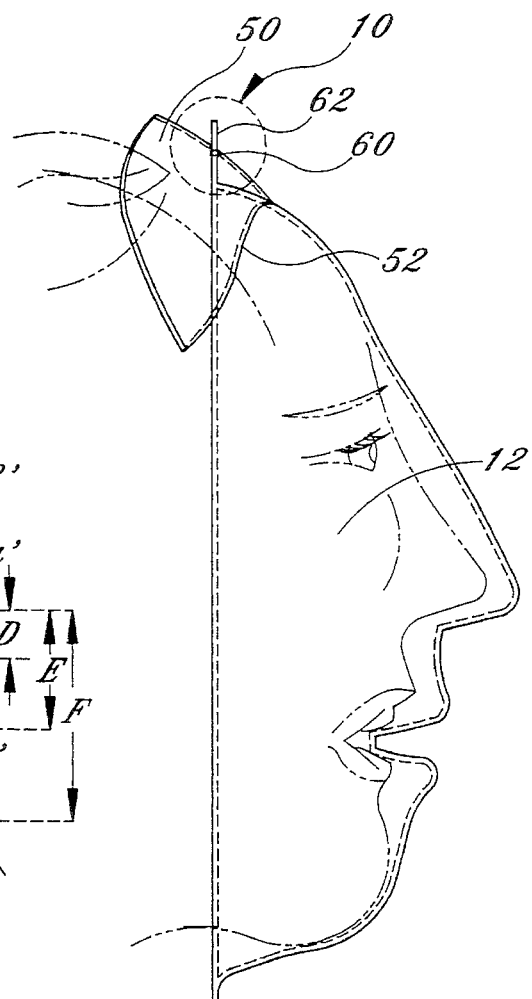
FIG. 9 is a cross sectional elevational view taken along lines 9—9 of FIG. 8.

In a further embodiment shown in FIGS. 8—10, a forehead cover or protector 50 is employed which is connectable to the face shield body 12 near the top or forehead area thereof. The forehead cover 50 is preferably comprised of the same or similar material that the face shield body 12 is manufactured from for ease of production and use. Since the end user may wish to trim the cover 50, it may be advantageous to manufacture the cover 50 out of a thinner material such as 0.010" thick plastic. The forehead cover 50 is defined by a curved bottom edge 52 adapted to mate with the forehead area of the mask body 12, a top edge 54, and preferably generally curved left and right side edges 56, 58, respectively. The forehead cover 50 is curved to conform somewhat to the ordinary curvature of a human forehead, but may be manufactured in an exaggerated size so that the end user may trim it to comfortably and effectively fit their head. The purpose of the forehead cover is to prevent hair spray from contacting the sprayer's forehead where the mask 10 is too short and/or wide to reach the wearer's hairline, temple, and eyes.

Any acceptable fastening structure may be employed to connect cover 50 to mask body 12. In one embodiment, a slit 60 is provided in the forehead cover 50 to accommodate a connecting tab 62 which is attached to the face shield body 12. Tab 62 is, preferably, made generally resilient by the provision of a V-shaped notch 64 or other similar structure so that the tab 62 will be held in place through slit 60 in the manner of an umbrella clip. Notch 64 enables the pie-shaped members 62a and 62b to move toward one another as the forehead cover 50 is moved in position thereabout by sliding tab 62 into slit 60. It is important that the width of slit 60 be less than the distance between the points and 65 of tab 62, as shown in FIG. 10, so that the tab 62 cannot be removed from slit 60 without manipulating the pie-shaped members 62a and 62b. More than one such connecting arrangement may be employed, which will add stability to the connection. For instance, the tab 62 may be integrally formed with the shield 10 near the shield's top end in the area where the slit 60 would otherwise be located.

Figure 14:
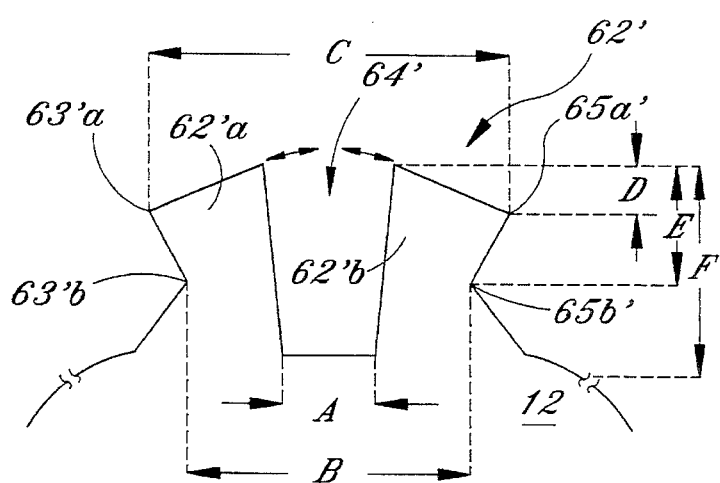
FIG. 14 is an enlarged view of an alternate embodiment of the area of detail indicated by circle "10" of FIG. 9.

Another fastening structure is seen in FIG. 14, which comprises a connecting tab 62' either attached to the face shield body 12 through slit 60 or formed as an integral piece. In the preferred embodiment, the tab 62' includes two hooks 62a' and 62b' which preferably have edges that are not perpendicular to the flange or main body of the tab 62'. However, the hooks 62a' and 62b' may and typically are somewhat parallel to an imaginary vertical plane with respect to the shield 10. Tab 62' is made generally resilient by the provision of a U-shaped notch 64' defined by diverging edges as outlined by tab members or hooks 62a' and 62b'. The notch 64' is typically 0.125 inches wide at its lower end which is referenced by distance "A". This distance allows the hooks 62a' and 62b' to deflect inward a sufficient distance so as to provide enough clearance for mounting attachments such as the cover 50 or hair net 100 to the forehead area of the shield 10 and/or the cheek guard 70 or the ear cover 90 to the cheek area. The distance "A", however, may differ so long as enough resiliency is provided for overcoming the mating apertures defined by either the shield slit 60 or the attachments. The hooks 62a' and 62b' return to their relaxed positions once an attachment is made. Therefore, it is important that the width of the tab 62' between the points 63a' and 65a', as shown in FIG. 14, be greater than the slit 60 or attachment aperture opening so that the tab 62' or attachment cannot be removed without manipulating the hooks 62a' and 62b'. In the preferred embodiment, the distance between the hook end points 63a' and 65a' typically 0.50 inches as referenced by "B" while the distance between the inner hook points 63b' and 65b' is normally 0.375 inches as referenced by "C", to ensure secure attachments. Other relevant distances are shown in FIG. 14 by "D","E", and "F" which are generally 0.0625 inches, 0.125 inches and 0.250 inches, respectively. It is important to note that these dimensions as represented by characters "A" through "F" are in no way limiting and may be adjusted without departing from the scope and spirit of the invention. Furthermore, additional connecting arrangements 62' and/or 62 may be employed for adding stability to the connections.

The particular configuration shown in FIGS. 8–10 of the forehead cover 50 causes at least three points of contact between the forehead cover 50 and face shield body 12, producing a steady, yet flexible, arrangement that can be utilized by individuals with virtually any size face. The top edge 54 of the cover may be trimmed as needed for custom fitting user's head contour.

Any coupling arrangement may be used to connect the forehead cover 50 to the face shield body 12, such as hook and loop material, snaps, etc. The arrangement shown is considered to be the best mode contemplated by the inventor at this time, but is certainly not intended to limit the scope of the invention.

Figure 11:
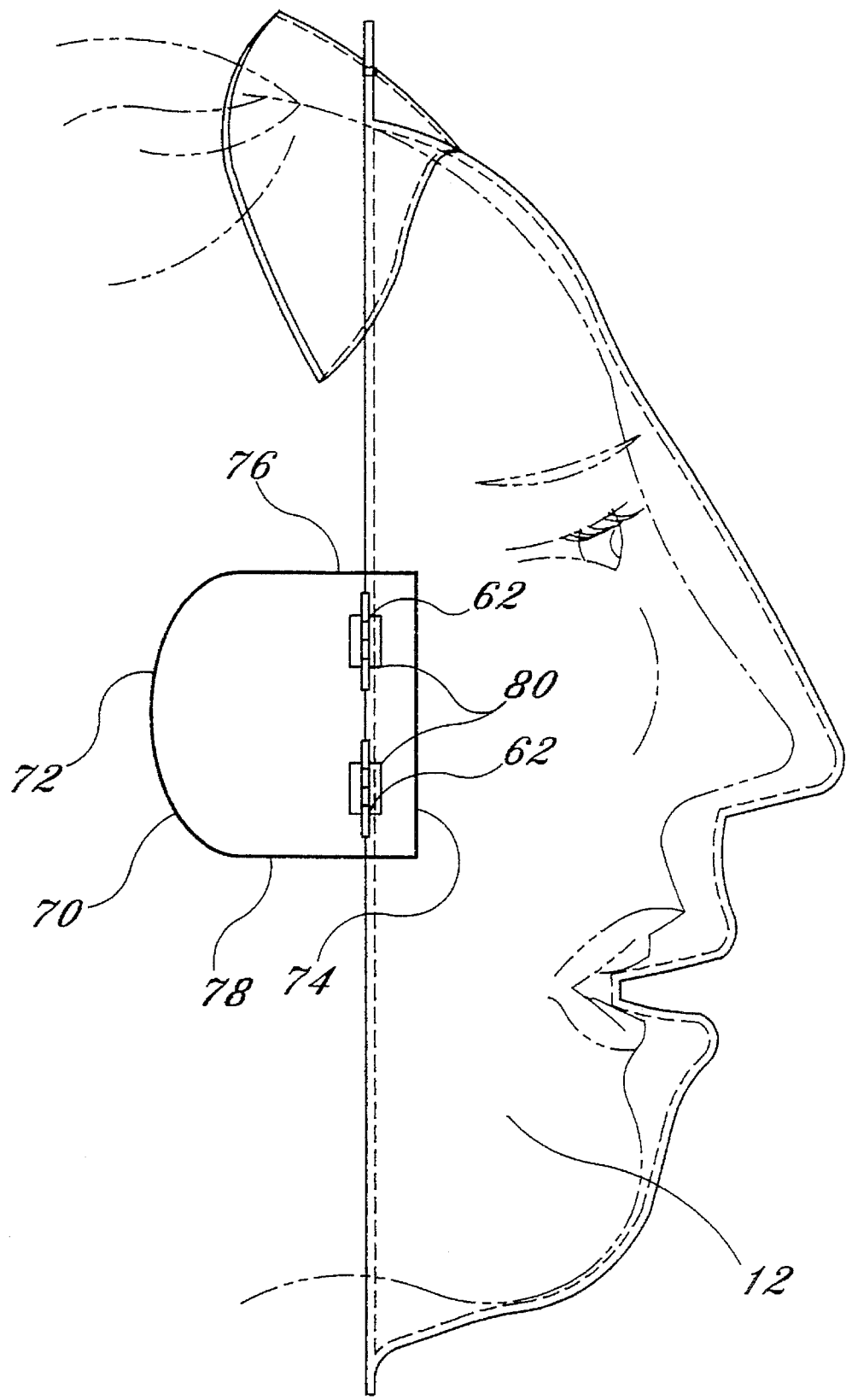
FIG. 11 is a cross sectional elevational view taken along lines 9—9 of FIG. 8 with a removable cheek guard connected thereto.

In yet another embodiment shown in FIG. 11, a cheek guard attachment 70 is incorporated which is releasably connectable to the side or cheek area of the face shield body 12. The cheek guard 70 provides an extension where the mask 10 is too small to reach over the cheeks to prevent hair spray from contacting the wearer's cheeks and protects clothes when they are pulled over the head. The cheek guard 70 is preferably manufactured from the same or similar material that the face shield body 12 is manufactured from for ease of production and so that it can flexibly deflect with the shape of the face. The cheek guard 70 is defined by a preferably curved side edge 72 adapted to comfortably rest on the a side edge 74 that engages the face shield body 12, a top edge 76, and a bottom edge 78. It should be noted that the cheek shield 70 may assume any reasonable shape without departing from the scope and spirit of the invention. Also, the guard 70 may be made of fabric or any other suitable material which will carry out the objectives stated herein.

As the preferred way of connecting cheek guard 70 to mask 12, but not by way of limitation. Two slits 80 are provided in the cheek guard 70 to individually accommodate connecting tabs 62 which are attached to the face shield body 12 as previously discussed. Tab 62, or umbrella clip, is generally resilient by the provision of a V-shaped notch 64 or other similar cutout so that the pie-shaped members 62a and 62b deflect inward when attaching the cheek shield 72 through the slits 80. The notch 64 and slots 66 and 68 enable the pie-shaped members 62a and 62b to move inward toward one another as the slits 80 are mounted over the tabs 62. It should be further noted that other attachment arrangements may be employed to connect the cheek guard 70 to the face shield body 12, such as hook and loop material, snaps, etc.

Figure 12:
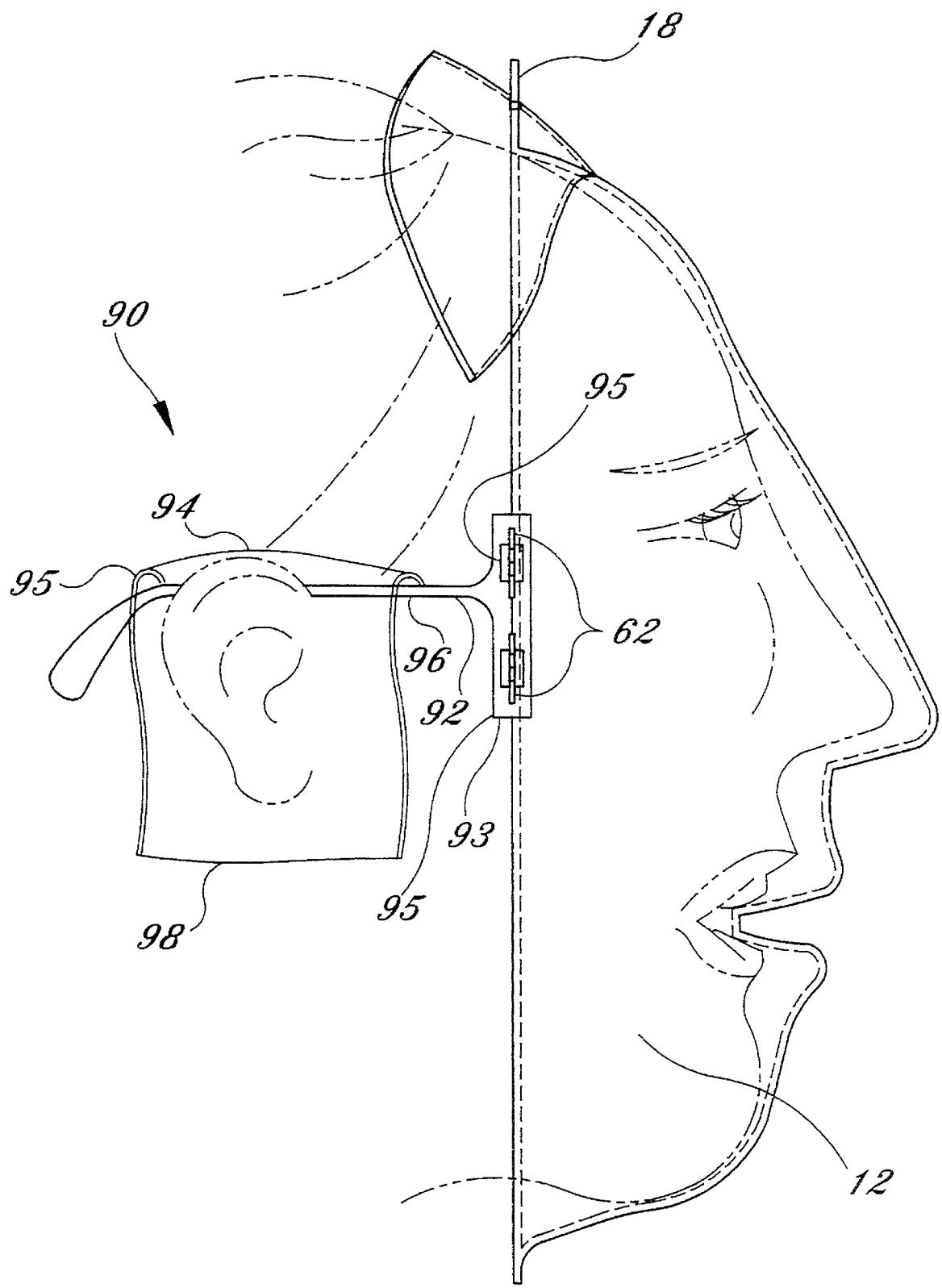
FIG. 12 is a cross sectional elevational view taken along lines 9—9 of FIG. 8 with a removable ear cover connected thereto.

In yet a further embodiment shown in FIG. 12, an ear guard attachment 90 is releasably connected to the side of the face shield body 12 so as to cover and protect the ears of the wearer. The ear guard 90 prevents spray from entering a wearer's ears without having to shield the ear with a hand, so that both hands may be dedicated to grooming the hair. The ear guard 90 is preferably manufactured from the same or similar material that the face shield body 12 is manufactured from for ease of production, flexibility, and use.

The ear guard 90 comprises a semi-flexible, yet semi-rigid support arm 92, such as that used with eyeglasses, for engaging the ear and a flexible ear cover 94 connected to the arm 92 for draping over the ear to provide protection. The arm 92 directly clips to the side of the face shield body 12 by way of fasteners as banana clips, hooks, umbrella clip tabs 62 as previously discussed, or any other suitable fastener. To support the ear guard protector 90 with an umbrella clip or clips 62, a slit or slits 95 may be defined by the arm fastener 93 for receiving the tabs 62. Beginning at the distal end 95 of the arm 92 and extending across the arm 92 toward the fastener 93, the ear cover 94 may be permanently or removably affixed to the arm 92. The ear cover 94 typically stops short of the fastener 93 but may extend substantially close to the fastener 93 to cover the cheek as well.

The ear cover 94 extends from the arm 92 up over the ear, draping downward beneath the earlobe. The ear cover 94 may be custom trimmed by the user to a desired shape or length. The arm 92 must be flexible enough to accommodate resting on the ear while being rigid and strong enough to support the weight of the ear cover 94. The arm 92 may be curved at its free end for curling around the ear to provide additional support for the face shield body 12. Accordingly, the arm 92 necessitates manufacturing from a plastic strong enough to support the ear cover 94 and yet flexible enough for deflecting when adjusting the arm 92 to rest on top of the ear.

Figure 13:
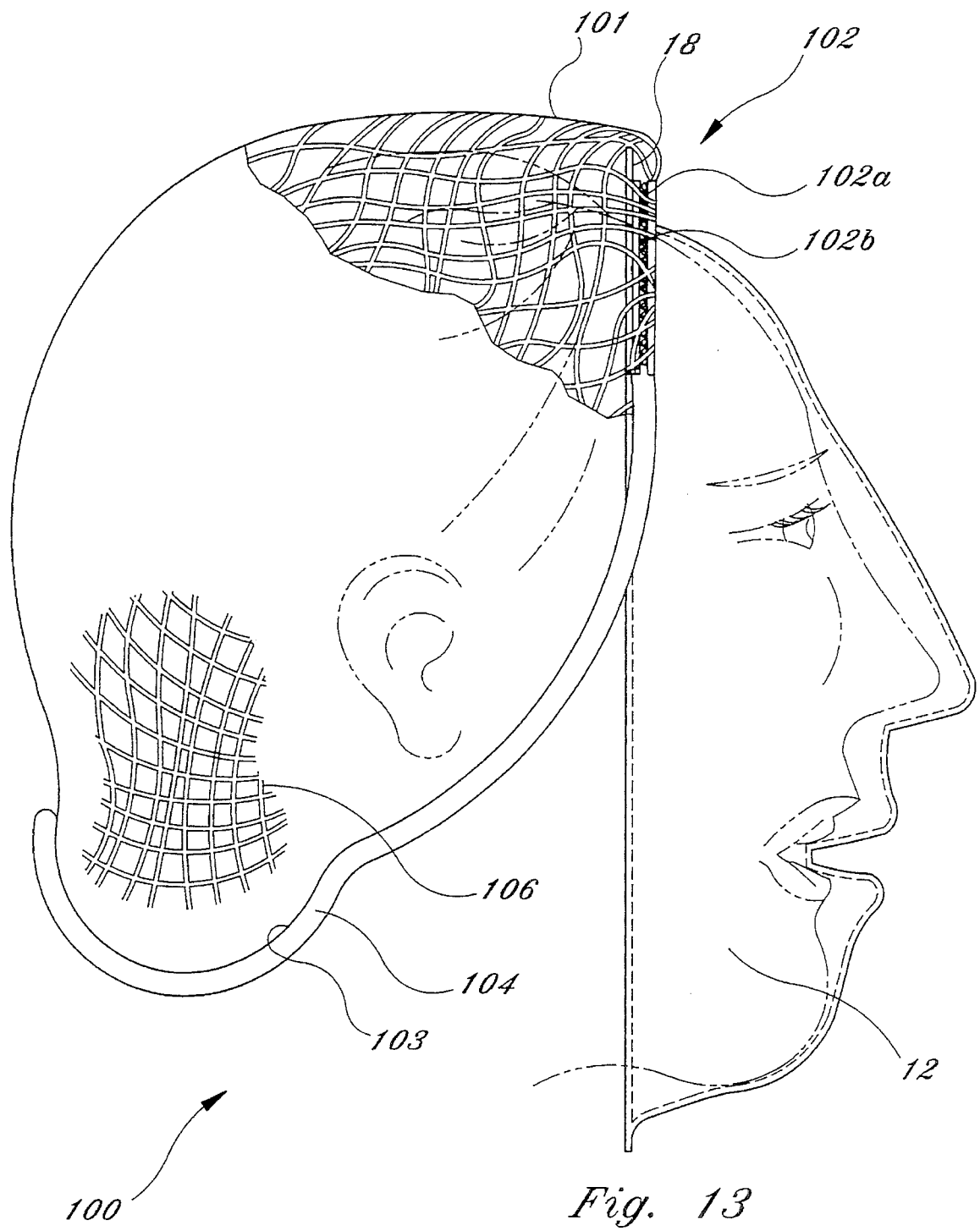
FIG. 13 is a cross sectional elevational view taken along lines 9—9 of FIG. 8 with a removable hair net connected thereto.

In a final embodiment shown in FIG. 13, a hair cover 100 is employed which is connectable to the top of the face shield body 12, depending downward for covering the user's hair. The hair cover 100 is preferably a flexible fabric or net sheet comprised of a top portion 101, releasably attached to the top of the face shield body 12 around the portion of the peripheral edge 18 proximal the forehead. Elastic band 104 may be affixed or sewn to the peripheral edge 103 of the hair cover which depends from the mask 12. The elastic band 104 is connected to the edges of the hair cover 100 to permit the user to place the hair cover over his or her hair to prevent pulled-over clothing from affecting styled hair. The hair cover 100 is defined by a mesh of fabric material 106 which flexibly covers the hair without jeopardizing time spent grooming the hair. Thus, only the top portion 101 of the hair cover 100 is connected to the top of the face shield body 12, while the remainder of the hair cover 100 is free to be stretched over the styled hair. The hair cover 100 may be removably attached to the face shield body 12 by way of umbrella clips, such as those referenced by numeral 62, or by any other suitable securing structure. With the hook and loop attachment 102 shown in FIG. 13, a hook and loop strip 102a may be permanently affixed to an interior portion of a portion of the peripheral edge 103 of cover 100 adjacent the forehead area of mask 12 or may be attached to elastic band 104. A corresponding hook and loop strip 102b may likewise be permanently attached to the exterior portion of mask peripheral edge 18 in the area of the forehead. The elastic band 104 maintains the position of the hair cover 100 over the hair.

The instant invention has been shown and described herein in what are considered to be the most practical and preferred embodiments. It is recognized, however, that reasonable departures may be made therefrom within the spirit and scope of the invention, and that obvious modifications will occur to those persons skilled in the art.

What is claimed is:

1. In a face shield defined as a flexible, deformable, transparent, generally concave shell adapted to conform to at least a portion of the contour of a wearer's face, said shell defining interior and exterior surfaces and having a mouthpiece projecting inwardly from the interior surface of the shell, the mouthpiece adapted to be grasped between a wearer's teeth after the shield is sealingly conformed to at least a portion of a wearer's face for maintaining engagement between the shell and a wearer's face, the improvement comprising:

a generally flexible C-shaped forehead cover member, releasably attachable to an upper end of said shield, said forehead cover defining a generally curved lower edge adapted to contact a curved forehead area defined by the exterior surface of the shell.

2. The face shield of claim 1, wherein said forehead cover is generally C-shaped when viewed from above and is generally rectangular in cross section.

3. The face shield of claim 1, further comprising means for connecting said forehead cover to said upper end of said shield.

4. The face shield of claim 3, wherein said means for connecting said forehead cover is comprised of at least one resilient tab extending from the upper end of said shield and a corresponding at least one aperture defined by said forehead cover for receiving said at least one tab.

5. The face shield of claim 1, further comprising at least one generally flexible cheek cover member for covering at least one cheek of a wearer's face when the face shield is too small to do so, said cheek cover member releasably attachable to a side edge of said shield and extending from said side edge.

6. The face shield of claim 5, further comprising means for connecting said cheek cover member to said side edge of said shield.

7. The face shield of claim 6, wherein said means for connecting cheek cover member is comprised of at least one resilient tab extending from said side edge of said shield and a corresponding at least one aperture defined by said cheek member for receiving said tab.

8. The face shield of claim 1, further comprising at least one generally flexible ear cover member for covering at least one ear of a wearer's face, said at least one ear cover member comprising:

a support arm releasably attachable to a side edge of said shield at one end of said support arm, said support arm extending outward from said side edge when attached; and a flexible ear drape connected to said support arm for draping over the at least one ear, said support arm having a distal end for engaging a wearer's ear to support said ear drape.

9. The face shield of claim 8, further comprising means for connecting said ear cover member to said side edge of said shield.

10. The face shield of claim 9, wherein said means for connecting said ear cover member is comprised of at least one resilient tab extending from said side edge of said shield and a corresponding at least one aperture defined by said support arm at one end of said support arm for receiving said resilient tab.

11. The face shield of claim 1, further comprising a generally stretchable hair cover member for covering a wearer's hair, said hair cover member having an elastic circumferential edge and a portion of said elastic circumferential edge releasably attachable to an upper end of said shield.

12. The face shield of claim 11, further comprising means for connecting said hair cover member to said upper end of said shield.

13. The face shield of claim 12, wherein said means for connecting said hair cover member is comprised of at least one hook and loop strip attached to said upper end of said shield and a corresponding at least one hook and loop strip attached to said portion of said circumferential edge which is attachable to said upper end of said shield.

14. In a face shield defined as a flexible, deformable, transparent, generally concave shell adapted to conform to at least a portion of the contour of a wearer's face, said shell defining interior and exterior surfaces and having a mouthpiece projecting inwardly from the interior surface of the shell, the mouthpiece adapted to be grasped between a wearer's teeth after the shield is sealingly conformed to at least a portion of a wearer's face for maintaining engagement between the shell and a wearer's face, the improvement comprising:

at least one generally flexible cheek cover member for covering at least one cheek of a wearer's face when the face shield is too small, said cheek cover member releasably attachable to a side edge of said shield and extending from said side edge; and means for connecting said cheek cover member to said side edge of said shield.

15. The face shield of claim 14, wherein said means for connecting said cheek cover member is comprised of at least one resilient tab extending from said side edge of said shield and a corresponding at least one aperture defined by said cheek cover member for receiving said tab.

16. In a face shield defined as a flexible, deformable, transparent, generally concave shell adapted to conform to at least a portion of the contour of a wearer's face, said shell defining interior and exterior surfaces and having a mouthpiece projecting inwardly from the interior surface of the shell, the mouthpiece adapted to be grasped between a wearer's teeth after the shield is sealingly conformed to at least a portion of a wearer's face for maintaining engagement between the shell and a wearer's face, the improvement comprising:

at least one generally flexible ear cover member for covering at least one ear of a wearer's face, said at least one ear cover member including a support arm releasably attachable to a side edge of said shield at one end of said support arm and a flexible ear drape connected to said support arm for draping over at least one ear, said support arm extending outward from said side edge when attached, said support arm having a distal end for engaging a wearer's ear to support said ear drape; and means for connecting said ear cover member to said side edge of said shield.

17. The face shield of claim 16, wherein said means for connecting said ear cover member is comprised of at least one resilient tab extending from said side edge of said shield and a corresponding at least one aperture defined by said support arm at said one end of said support arm for receiving said resilient tab.

18. In a face shield defined as a flexible, deformable, transparent, generally concave shell adapted to conform to at least a portion of the contour of a wearer's face, said shell defining interior and exterior surfaces and having a mouthpiece projecting inwardly from the interior surface of the shell, the mouthpiece adapted to be grasped between a wearer's teeth after the shield is sealingly conformed to at least a portion of a wearer's face for maintaining engagement between the shell and a wearer's face, the improvement comprising:

a generally flexible hair cover member for covering a wearer's hair, said hair cover member having a circumferential edge and a portion of said circumferential edge releasably attachable to an upper end of said shield; and means for connecting said hair cover member to said upper end of said shield.

19. The face shield of claim 18, wherein said means for connecting said hair cover member is comprised of at least one hook and loop strip attached to said upper end of said shield and a corresponding at least one hook and loop strip attached to said portion of said circumferential edge which is attachable to said upper end of said shield.

* * * * *